United States Patent
Chen et al.

(10) Patent No.: US 11,634,776 B2
(45) Date of Patent: Apr. 25, 2023

(54) METHOD FOR DIAGNOSIS AND SUBTYPING OF ADULT ONSET STILL'S DISEASE

(71) Applicant: CHINA MEDICAL UNIVERSITY, Taichung (TW)

(72) Inventors: Der-Yuan Chen, Taichung (TW); Chin-An Yang, Hsinchu County (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 230 days.

(21) Appl. No.: 16/897,295

(22) Filed: Jun. 10, 2020

(65) Prior Publication Data

US 2021/0388439 A1    Dec. 16, 2021

(51) Int. Cl.

| | |
|---|---|
| *G01N 33/68* | (2006.01) |
| *G01N 33/49* | (2006.01) |
| *G01N 33/48* | (2006.01) |
| *G01N 33/50* | (2006.01) |
| *G01N 33/53* | (2006.01) |
| *C12Q 1/6883* | (2018.01) |
| *C12Q 1/68* | (2018.01) |
| *C12Q 1/6813* | (2018.01) |

(52) U.S. Cl.
CPC ....... *C12Q 1/6883* (2013.01); *G01N 33/6863* (2013.01); *G01N 33/6869* (2013.01); *C12Q 1/68* (2013.01); *C12Q 1/6813* (2013.01); *C12Q 2600/106* (2013.01); *C12Q 2600/112* (2013.01); *C12Q 2600/158* (2013.01); *G01N 33/48* (2013.01); *G01N 33/49* (2013.01); *G01N 33/50* (2013.01); *G01N 33/53* (2013.01); *G01N 2333/525* (2013.01); *G01N 2333/54* (2013.01); *G01N 2333/912* (2013.01); *G01N 2800/7095* (2013.01)

(58) Field of Classification Search
CPC ...... G01N 33/6869; G01N 33/49; C12Q 1/68; C12Q 2600/112; C12Q 2600/158
See application file for complete search history.

(56) References Cited

U.S. PATENT DOCUMENTS

2012/0308564 A1* 12/2012 Bayliffe .................... A61P 3/10
424/133.1

OTHER PUBLICATIONS

Ghafouri-Fard "Myocardial infarction associated transcript (MIAT): review of its impact in the tumorigenesis" (Biomedicine & Pharmacotherapy 2021 133: 111040). (Year: 2021).*
Eftekharian "Expression analysis of long non-coding RNAs in the blood of multiple sclerosis patients" (J. Mol. Neurosci 2017 63:333) (Year: 2017).*
Li "The long noncoding RNA THRIL regulates TNFalpha expression through its interaction with hnRNPL" (PNAS 2014 111:1002). (Year: 2014).*
Liu "Long non-coding RNA THRIL promotes LPS-induced inflammatory injury by down-regulating micrRNA-125b in ATDC5 cells" (International Immuopharmacology 2019 66:354). (Year: 2019).*

* cited by examiner

*Primary Examiner* — Changhwa J Cheu
(74) *Attorney, Agent, or Firm* — Hannah Tien

(57) ABSTRACT

The invention relates to method of diagnosis a subject suffering from Adult-onset Still's disease and further to determine the disease course of the subject suffering from Adult-onset Still's disease.

6 Claims, 10 Drawing Sheets
Specification includes a Sequence Listing.

a b

METHOD FOR DIAGNOSIS AND SUBTYPING OF ADULT ONSET STILL'S DISEASE

This application contains a Sequence Listing in a computer readable form, the file name is 3403-CMU-SEQListing-ST25, created on Aug. 18, 2020, the size is 3 KB, which is incorporated herein by reference.

BACKGROUND OF THE INVENTION

Field of the Invention

The invention relates to a method for diagnosis and subtyping of adult-onset Still's disease a subject suffering from Adult-onset Still's disease.

Description of Prior Art

Adult-onset Still's disease (AOSD), an autoinflammatory disorder, is characterized by fever, rash, arthralgia or arthritis, multisystemic involvement, and elevated levels of acute phase reactants. Due to persistent spiking fever, the diagnosis is usually delayed. Most patients are diagnosed only after secondary symptoms appear and more common conditions are excluded, such as infection or other malignant diseases. Despite these difficulties, the Yamaguchi criteria provides the highest sensitivity and accuracy for AOSD diagnosis in the current clinical diagnosis.

It is also marked by elevated levels of type 17 T helper (Th17)-related cytokines and proinflammatory cytokines such as tumor necrosis factor (TNF)-$\alpha$, interleukin (IL)-1$\beta$, IL-6, IL-8 and IL-18; however, the exact pathogenesis remains elusive. An association of virus infection with AOSD is recently reported. Previously studies have also revealed an elevated expression of NLRP3-inflammasome in AOSD patients. In addition, increased circulating microRNA-134, probably up-regulated by toll-like receptor (TLR)-3 ligand (poly I:C), was observed in AOSD patient, with the levels positively correlated with disease activity. Despite such evidence, diagnostic markers are still lacking, and the diagnosis of AOSD is usually made by clinical criteria.

Disease course of AOSD may vary considerably and can be divided into two main subtypes with different prognoses: systemic and articular subtype. Systemic subtype is characterized by predominantly systemic features, while articular subtype by severe articular manifestations mimicking rheumatoid arthritis (RA). Although proinflammatory cytokines contribute to AOSD pathogenesis, they are of limited use for predicting disease course because of the broad overlap between the subtypes. Several investigators including us have revealed significantly higher TNF-$\alpha$ levels in patients with articular subtype AOSD, for whom biologics targeting TNF-$\alpha$ have been proved effective in the treatment From mild to severe manifestations, disease course in AOSD is difficult to evaluate. Therefore, accurate evaluate of disease course is important for treatment decisions. Certain acute phase reactants, including C-reactive protein and ferritin, are used in laboratories to monitor AOSD disease activity. However, these markers are non-specific and do not correlate well with disease course. Pouchot score can be used to assess disease course, including elevated liver enzymes, pericarditis, myalgia, neutropenia, and lymphadenopathy.

For AOSD treatment, the first-line treatment of AOSD are non-steroidal anti-inflammatory drugs (NSAIDs) and glucocorticoids. The second-line therapies, including synthetic disease modifying anti-rheumatic drugs (DMARDS) and biologic agents, are administered after the lack of clinical response to first-line treatment. DMARDS, such as methotrexate, azathioprine, and leflunomide, are often used to reduce the quantity of corticosteroids being administered. The biologic agents, including intravenous immunoglobulin, anti-TNF-$\alpha$ drugs, such as etanercept, infliximab and adalimumab, as well as anti-IL-6 agents, i.e., tocilizumab, also appear to adequately control the disease in non-responders to conventional therapy.

Long non-coding RNAs (lncRNAs), the non-protein-coding transcripts greater than 200 nucleotides in length, have emerged as novel players in different stages of gene regulation. LncRNAs are involved in chromatin remodeling, transcription process and cellular response through RNA-DNA, RNA-RNA or RNA-protein interactions. Recent studies also revealed that lncRNAs can be induced in immune cells and act as the key regulators of inflammatory responses. In addition, lncRNAs have been implicated in innate immunity against virus infection. Although increasing number of lncRNAs are being discovered, their biologic functions and mechanisms of action are largely unknown.

The present invention had particular interests in six lncRNAs which are related to immune regulation or inflammatory response and might be involved in pathogenesis of AOSD or virus infection [3-10,20-22]. The six lncRNAs are MIAT (10.18 kb, NONHSAT192181.1), THRIL (1.98 kb, NONHSAT164169.1), NTT (17.57 kb, NONHSAT115106.2), RMRP (0.27 kb, NONHSAT130962.2), PACERR (0.83 kb, NONHSAT150184.1), and NEAT1 (22.74 kb, NONHSAT022112.2). MIAT (myocardial infarction associated transcript) is known to be involved in the pathogenesis of a variety of diseases, including myocardial infarction, microvascular dysfunction, and myalgic encephalomyelitis/chronic fatigue syndrome (ME/CFS). THRIL (TNF$\alpha$ and hnRNPL-related immunoregulatory lincRNA) acts as a scaffold through interacting with heterogeneous nuclear ribonucleoprotein L (hnRNPL), and this complex binds to TNF-$\alpha$ promoter to induce its transcription following TLR2 activation. NTT (non-coding transcript in T cells) is discovered in activated CD4$^+$ T cells stimulated with human immunodeficiency virus (HIV) peptides, suggesting its role in adaptive immunity. Previously study showed NTT is a regulator of inflammation in monocytes, and its activation participates in monocytes/macrophages differentiation and contributes to the pathogenesis of rheumatoid arthritis (RA). RMRP (RNA component of the mitochondrial RNA-processing endoribonuclease) promotes ROR$\gamma$tDDX5 assembly and is recruited to ROR$\gamma$t-occupied genomic loci of critical genes implicated specifically in the Th17 effector program. PACERR (p50-associated COX-2 extragenic RNA, also known as PACER), is a positive regulator of COX-2 expression in human epithelial cells and macrophage-like cells after TLR4 activation. NEAT1 (nuclear enriched abundant transcript 1) is essential for the formation of nuclear body paraspeckles, which facilitate IL-8 transcriptional activation. NEAT1 expression is also increased after the stimulation of TLR3 ligand, poly(I:C), a synthetic analogue of double strand RNA representing active viral infection. However, there has been no research data about the expression of circulating lncRNAs in AOSD patients.

In the present invention, the expression signatures and potential diagnostic values of the six lncRNAs in AOSD patients are investigated. Patients with rheumatoid arthritis (RA) and systemic lupus erythematosus (SLE) as disease controls are also enrolled. The effects of TLR3 ligand poly(I:C) and TLR4 ligand LPS on lncRNA expressions were also evaluated in a human monocytic cell line THP-1. In addition, predictive scores derived from the expression levels of lncRNAs and proinflammatory cytokines were established for AOSD diagnosis and disease course prediction.

SUMMARY OF THE INVENTION

The present invention relates to a method for detecting or diagnosing a subject suffering from Adult-onset Still's disease, the method comprising the steps of: (a) providing a blood sample and a peripheral blood mononuclear cell from a subject; (b) detecting the expression level of a protein biomarker in the blood sample, wherein the protein biomarker is IL-18; (c) calculating a A score of the detected IL18, MIAT and THRIL obtained in step (b) through a prediction equation, which is determined by performing a multiple regression analysis; and (d) comparing the A score calculated in step (c) with a cutoff value, wherein the cutoff value is obtained by a Receiver Operator Characteristic (ROC) method, wherein the cutoff value corresponds to when AUC (the area under an ROC curve) reached at its maximum, wherein the score being higher than the cutoff value indicates that the subject suffering from Adult-onset Still's disease.

In one aspect, the present invention relates to a method for determining a disease course of a subject suffering from Adult-onset Still's disease, the method comprising the steps of: (a) providing a blood sample and a peripheral blood mononuclear cell, which are collected from the subject suffering from Adult-onset Still's disease; (b) detecting the expression level of a protein biomarker in the blood sample, wherein the protein biomarker is TNFα; detecting expression levels of a long non-coding ribonucleic acid (lncRNA) from the peripheral blood mononuclear cell, wherein the lncRNA is NTT; (c) calculating a B score of the detected TNFα and NTT obtained in step (b) through a prediction equation, which is determined by performing a multiple regression analysis; and (d) comparing the score calculated in step (c) with a cutoff value, which is obtained by a Receiver Operator Characteristic (ROC) method, wherein the cutoff value corresponds to when AUC (the area under an ROC curve) reached at its maximum, wherein the score being higher than the cutoff value indicates that the subject suffering from the disease course of Adult-onset Still's disease is a systemic subtype or an articular subtype.

In another aspect, the present invention relates to a kit for diagnosing a subject suffering from Adult-onset Still's disease, wherein the kit comprises a reagent selected from the group consisting of: (a) a reagent for detecting a IL-18 protein; (b) a reagent for detecting lncRNAs of MIAT and THRIL; and (c) an instruction manual, providing a prediction equation and a cutoff value for determining whether the subject suffering from adult-onset Still's disease.

In still yet another aspect, the present invention relates to a kit for diagnosing disease course of a subject suffering from Adult-onset Still's disease, wherein the kit comprises a reagent selected from the group consisting of: (a) a reagent for detecting a TNFα protein; (b) a reagent for detecting a lncRNA of NTT; and (c) an instruction manual, providing a prediction equation and a cutoff value for determining whether the subject suffering from the disease course of Adult-onset Still's disease is a systemic subtype or an articular subtype.

DETAILED DESCRIPTION OF THE INVENTION

Figure 1:
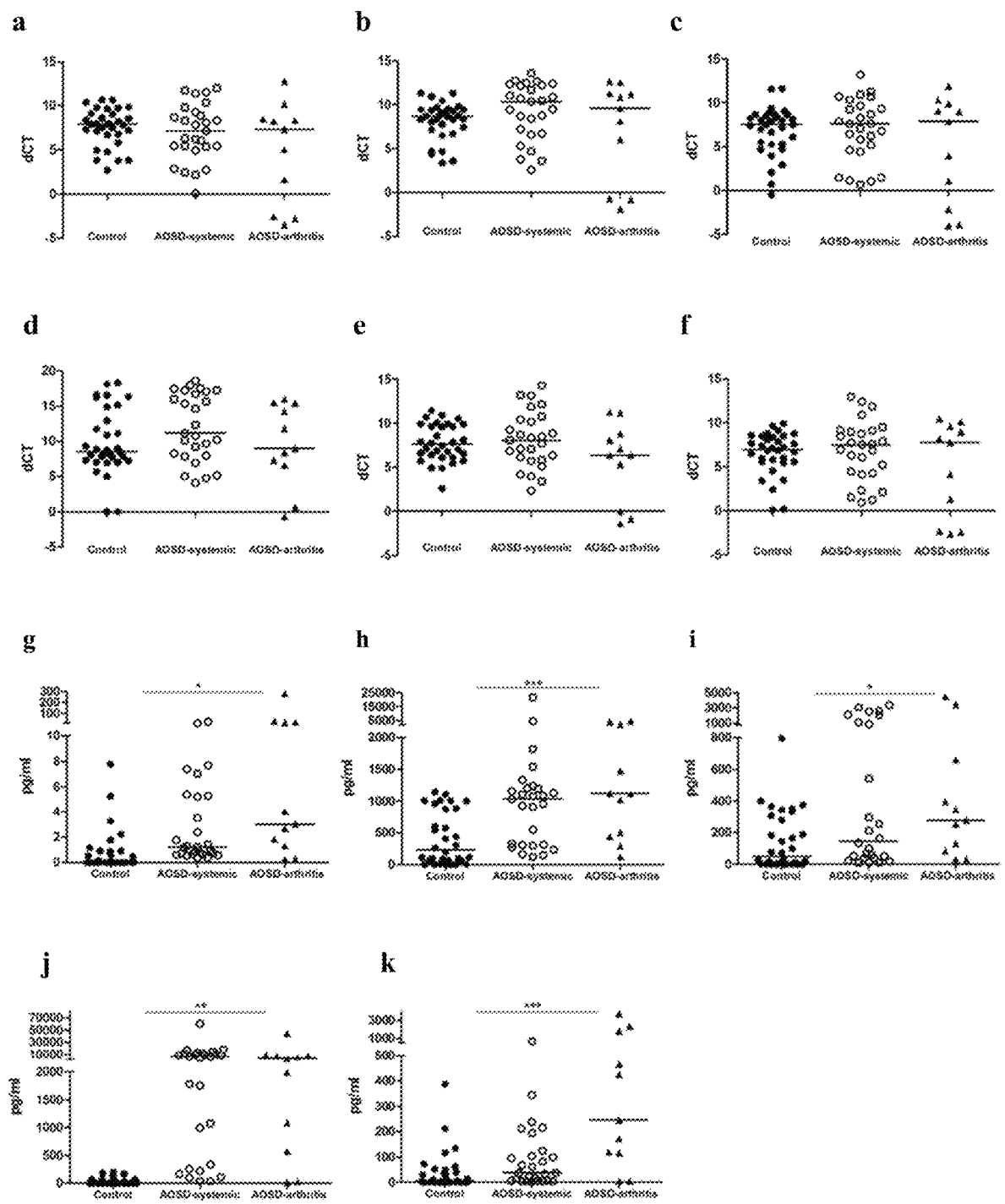
FIG. 1. Expression profile of lncRNAs and cytokines in AOSD patients and healthy controls. a-f. Delta CT (dCT, $CT_{lncRNA\ gene}-CT\ GAPDH$) levels of each lncRNA on PBMCs derived from healthy controls (Control), AOSD-systemic subtype patients (AOSD-systemic), and AOSD-arthritis subtype patients (AOSD-arthritis). a: MIAT, b: THRIL, c: NTT, d: NEAT1, e: RMRP, f: PACERR. g-k. Plasma cytokine levels detected in healthy controls, AOSD-systemic subtype patients, and AOSD-arthritis subtype patients. g: IL-1p, h: IL-6, i: IL-17A, j: IL-18, k: TNF-α. Lines represent medians. *: $p<0.05$, : $p<0.01$, *: $p<0.001$ calculated by Kruskal-Wallis tests.

The present invention relates to a method for detecting or diagnosing a subject suffering from Adult-onset Still's disease, the method comprising the steps of: (a) providing a blood sample and a peripheral blood mononuclear cell from a subject; (b) detecting the expression level of a protein biomarker in the blood sample, wherein the protein biomarker is IL-18; (c) calculating a A score of the detected IL18, MIAT and THRIL obtained in step (b) through a prediction equation, which is determined by performing a multiple regression analysis; and (d) comparing the A score calculated in step (c) with a cutoff value, wherein the cutoff value is obtained by a Receiver Operator Characteristic (ROC) method, wherein the cutoff corresponds to when AUC (the area under an ROC curve) reached at its maximum, wherein the score being higher than the cutoff value indicates that the subject suffering from Adult-onset Still's disease.

In the above method, the method further comprises the step of (e) administering an effective amount of AOSD-treating drug to the subject.

In one embodiment, the prediction equation is:

$$A\ score = 1.62*THRIL\Delta CT - 1.43*MIAT\Delta CT + 0.02*IL\text{-}18\ (pg/ml)$$

In other embodiment, the cutoff value is between 5.85 to 7.12, with sensitivity of 94.4%-100%, and specificity of 93.7-100%.

In another embodiment, the cutoff value of 7.114, with sensitivity of 94.87%, and specificity of 100%.

In the above method, the method further comprise detecting the expression level of PIK3CA in the peripheral blood mononuclear cells, wherein the PIK3CA gene expression is higher than a healthy individual indicates the subject is excluded from has systemic lupus erythematosus, rheumatoid arthritis or sepsis.

In the above method, the healthy individual is an individual who does not have rheumatic diseases.

In the above method, the method to detect the expression level of the protein biomarker in step (b) is an immunological assay.

In the above method, the method to detect the expression level of lncRNAs in step (b) is polymerase chain reaction.

In the above method, wherein the blood sample is whole blood, serum or plasma.

In another aspect, the present invention relates to a method for determining a disease course of a subject suffering from Adult-onset Still's disease, the method comprising the steps of: (a) providing a blood sample and a peripheral blood mononuclear cell, which are collected from the subject suffering from Adult-onset Still's disease; (b) detecting the expression level of a protein biomarker in the blood sample, wherein the protein biomarker is TNFα; detecting expression levels of a long non-coding ribonucleic acid (lncRNA) from the peripheral blood mononuclear cell, wherein the lncRNA is NTT; (c) calculating a B score of the detected TNFα and NTT obtained in step (b) through a prediction equation, which is determined by performing a multiple regression analysis; and (d) comparing the score calculated in step (c) with a cutoff value, which is obtained by a Receiver Operator Characteristic (ROC) method, wherein the cutoff value corresponds to when AUC (the area under an ROC curve) reached at its maximum, wherein the score being higher than the cutoff value indicates that the subject suffering from the disease course of Adult-onset Still's disease is a systemic subtype or an articular subtype.

In the above method, the method further comprises the step of (e) administering an effective amount of AOSD-treating drug to the subject.

In one embodiment, the prediction equation is:

$$B\ score = 0.22*NTT\Delta CT - 0.01*TNF\text{-}\alpha\ (pg/ml).$$

In other embodiment, the cutoff value is between 0.17 to 0.83 with sensitivity of 57.1%-71.4%, and specificity of 66.7-100%.

In another embodiment, the cutoff value of 0.266, with sensitivity of 66.7% and specificity of 90.9%.

In the above method, the method to detect the expression level of the protein biomarker in step (b) is an immunological assay.

In the above method, the method to detect the expression level of lncRNAs in step (b) is polymerase chain reaction.

In the above method, the blood sample is whole blood, serum or plasma.

In yet another aspect, the present invention relates to a kit for diagnosing a subject suffering from Adult-onset Still's disease, wherein the kit comprises a reagent selected from the group consisting of: (a) a reagent for detecting a IL-18 protein; (b) a reagent for detecting lncRNAs of MIAT and THRIL; and (c) an instruction manual, providing a prediction equation and a cutoff value for determining whether the subject suffering from adult-onset Still's disease.

In still yet a further aspect, the present invention relates to a kit for diagnosing disease course of a subject suffering from Adult-onset Still's disease, wherein the kit comprises a reagent selected from the group consisting of: (a) a reagent for detecting a TNFα protein; (b) a reagent for detecting a lncRNA of NTT; and (c) an instruction manual, providing a prediction equation and a cutoff value for determining whether the subject suffering from the disease course of Adult-onset Still's disease is a systemic subtype or an articular subtype.

Examples

Through the following specific embodiments, it can be further proved that the practical application scope of the present invention. It is only a preferred embodiment of the present invention, and does not limit the scope of the present invention. Therefore, any simple changes and modifications made in accordance with the scope of the present invention and the contents of the invention specification are still covered by the scope of the present invention.

Methods

Subjects: forty-one consecutive AOSD patients fulfilling the Yamaguchi criteria were enrolled. Patients with infections, malignancies or other rheumatic diseases were excluded (Table 1).

TABLE 1

| Criteria for the diagnosis of adult-onset Still's disease. Yamaguchi criteria | |
|---|---|
| Major criteria | Fever ≥ 39° C. lasting ≥ 1 week |
| | Arthralgia or arthritis lasting ≥ 2 weeks |
| | Typical nonpruritic salmon-colored rash |
| | Leukocytosis ≥ 10,000/mm³ with granulocytes ≥ 80% |
| Minor criteria | Sore throat |
| | Lymphadenopathy |
| | Abnormal liver function tests |
| | Negative tests for antinuclear antibody and rheumatoid factor |
| Exclusion criteria | Infection |
| | Malignancy |
| | Other rheumatic disease (vasculitis) |

Diagnostic requires:
At leat 5 criteria, including 2 major criteria and no exclusion criteria The systemic activity of each AOSD patient was assessed using a modified Pouchot score, with active AOSD defined as having an activity score of 4 or higher. This systemic activity score (range 0-12) assigns one point to each of 12 manifestations: fever, evanescent rash, sore throat, arthralgia or arthritis, myalgia, pleuritis, pericarditis, pneumonitis, lymphadenopathy, hepatomegaly or abnormal liver function, elevated leukocyte count ≥15,000/mm³, and serum ferritin levels >3000 µg/L.

At the study entry, all patients were treated with non-steroidal anti-inflammatory drugs with/without corticosteroids in an active status, but none received conventional synthetic disease-modifying anti-rheumatic drugs (csDMARDs) or biologic therapy. After investigation, 35 (85.4%) received at least one of csDMARDs including methotrexate (n=32), hydroxychloroquine (n=29), cyclosporine (n=15), and azathioprine (n=10). All the enrolled AOSD patients who were followed for at least one year were classified into two subtypes of disease course: a systemic subtype that includes the monocyclic and the polycyclic form, and the other articular subtype (persistent arthritis involving at least one joint and lasting longer than 6 months). Twenty patients fulfilling the 2010 classification criteria of the American College of Rheumatology (ACR)/European League Against Rheumatism (EULAR) collaborative initiative for RA and 20 patients fulfilling the 1997 revised criteria of the ACR for SLE were included as disease controls. Thirty-two age-matched healthy controls, who didn't have any rheumatic disease, were used as healthy controls. The Institutional Review Board approved this study (CMUH108-REC1-099), and each participant's written consent was obtained according to the Declaration of Helsinki.

RNA extraction and quantitative real-time PCR (qRT-PCR) for lncRNAs: around 8 ml of venous whole blood were drawn from a peripheral vein from the participants in the morning. Peripheral blood mononuclear cells (PBMCs) were immediately isolated using the Ficoll-Paque™ PLUS (GE Healthcare Biosciences, Illinois, USA) density gradient centrifugation. The PBMCs were stocked in a −80° C. refrigerator until for the simultaneous investigation of lncRNAs. Total RNAs from PBMCs were extracted by TRIzol® Reagent (Sigma-Aldrich, Missouri, USA) and purified using a RNeasy MinElute Cleanup kit (QIAGEN, Germany) according to the manufacturer's instructions.

Purified RNAs were quantified using an ND-1000 spectrophotometer (Nanodrop Technology, USA) at OD260 and 280 nm. Two patients who had low nucleic acid quality were excluded from further analysis. High Capacity cDNA Reverse Transcriptase Kit (ThermoFisher Scientific-Invitrogen, Waltham, Mass., USA) was used to reverse-transcribe 2 µg RNA into cDNA using for qRT-PCR analyses. Human glyceraldehyde 3-phosphate dehydrogenase (GAPDH) gene expression was used as an endogenous control. All primers were designed and synthesized by Genomics BioSci & Tech, Taipei, Taiwan. The following primer sequences were used as Table 2.

TABLE 2

Nucleotide sequence of oligonucleotides used for qRT-PCR.

| SEQ ID No. | Target | Sequence |
|---|---|---|
| 1 | MIAT-forward | 5'-CTGGAGAGGGAGGCATCTAA-3' |
| 2 | MIAT-reverse | 5'-AACTCATCCCCACCCACAC-3' |
| 3 | THRIL-forward | 5'-AACAGGTGCACGTTTCAGG-3' |
| 4. | THRIL-reverse | 5'-TACACATGATGGGACCCAAA-3' |
| 5 | NTT-forward | 5'-CTTGGCCTAAAAGGGGATG-3', |
| 6 | NTT-reverse | 5'-GCACCTTTGGTCTCCTTCAC-3' |
| 7 | RMRP-forward | 5'-AGAAGCGTATCCCGCTGAG-3' |
| 8 | RMRP-reverse | 5'-GAGAATGAGCCCCGTGTG-3' |
| 9 | PACERR-forward | 5'-TCCACGGGTCACCAATATAAA-3 |

TABLE 2-continued

Nucleotide sequence of
oligonucleotides used for qRT-PCR.

| SEQ ID No. | Target | Sequence |
|---|---|---|
| 10 | PACERR-reverse | 5'-CGTCCCTGCAAATTCTGG-3' |
| 11 | NEAT1-forward | 5'-CTCTGACCCGAAGGGTAGG-3' |
| 12 | NEAT1-reverse | 5'-CTGGCAGCTTTGCTCCTG-3' |
| 13 | PIK3CA-forward | 5'-TCA TGC ATT GTT TTG CAC CCC-3' |
| 14 | PIK3CA-reverse | 5'-AAT GGG ATA GTG CCT GAG CC-3' |
| 15 | GAPDH-forward | 5'-AGCCACATCGCTCAGACAC-3' |
| 16 | GAPDH-reverse | 5'-GCCCAATACGACCAAATCC-3' |

The qRT-PCR reactions were performed on the Roche LightCycler Instrument 480 using IQ2 TaqMan Probe qPCR system (Thermo Fisher Scientific, Massachusetts, USA). Real-time PCR using 40-200 ng cDNA was performed with one cycle of preincubation at 95° C. for 30 sec, 50 cycles of amplification (95° C. for 10 sec, 60° C. for 30 sec, 72° C. for 10 sec), and a final cooling at 40° C. for 30 sec. The difference of expression in the target gene relative to averaged internal control gene in each sample was calculated using the comparative threshold cycle (CT) method.

In vitro cell line studies: the human monocytic cell lines, TIP-1 cells (ATCC TIB-202; American Type Culture Collection, Rockville, Md.), were grown in lipopolysaccharide (LPS)-free RPMI medium (Gibco, ThermoFisher Scientific, USA) supplemented with 10% fetal bovine serum in an incubator containing 5% CO2 at 37° C. One million cells cultured in LPS-free RPMI medium were treated with Toll-like receptor (TLR) 3 ligand poly (I:C) (InvivoGen, California, USA) or TLR4 ligand LPS (Sigma-Aldrich, Merk, Darmstat, Germany) for 4 hours and 24 hours respectively. THP-1 cells cultured in LPS-free RPMI medium only for 4 hours and 24 hours were used as controls for the respective experiments. RNAs were then extracted from THP-1 cells for further qRT-PCR analyses. The difference in expression of the target gene relative to averaged internal control gene in each sample was calculated using the comparative threshold cycle (CT) method and evaluated by $\Delta$CT ($CT^{lncRNA}-CT^{GAPDH}$) The median $\Delta$CT value of multiple replicates of THP-1 cells in the control wells was calculated. The fold of expression of lncRNAs in THP-1 cells analyzed was calculated by $2^{-\Delta\Delta CT}$, which the $\Delta\Delta$CT calculated by the formula: [(CT lncRNA−CT GAPDH)−median $\Delta$CT of control replicates].

Determination of levels of proinflammatory cytokines: plasma cytokine levels were determined by the commercial ELISA kits for IL-1$\beta$ (RayBiotech Inc., Norcross, Ga., USA), IL-6 (PeproTech Inc., Rocky Hill, N.J., USA), IL-17A (RayBiotech Inc., Norcross, Ga., USA), IL-18 (Medical & Biology Laboratories Co, Ltd., Naka-Ku, Nagoya, Japan), and TNF-$\alpha$ (R&D Systems, Minneapolis, Minn., USA) according to each of the manufacturer's instructions. All assays were performed with both inter- and intra-assay coefficient of variation (CV) of less than 10%.

Bioinformatics and statistical analysis: the Kruskal-Wallis test was used via GraphPad Prism 5 to analyze the difference of lncRNAs and cytokine expression levels among AOSD patient subtypes and healthy control subjects. Multi-nominal regression analysis using the expression levels ($\Delta$CT) and plasma cytokine levels (pg/ml) as variables for diagnosing AOSD was performed by using the generalized linear model (glm) function of R software v.3.6.0 (R Foundation for Statistical Computing, Vienna, Austria). The lncRNA expression signature of each sample from AOSD patients and healthy controls were plotted on 3D-scatterplots by using R software to further visualize key variables separating AOSD patients from controls.

The AOSD cohorts were randomly divided into a test dataset (70% of the samples) and a validation dataset (30% of the samples), and a confusion matrix was built using the selected variables to summarize the performance of the classification algorithm (R software, glm function). AOSD prediction score were established by the combination of variables giving the best correct classification rates as analyzed by the aforementioned assays. Receiver operating characteristic curve (ROC) analysis was performed to determine the area under ROC curve (AUC), sensitivity, specificity, and accuracy using MedCalc v.14.

The Pearson's correlations were determined between lncRNA expression levels and proinflammatory cytokines or PIK3CA levels. Meta-analyses of the expression of the available lncRNA MIAT and IL-18 on transcriptomes of the other rheumatic diseases including RA and SLE were performed on the MetaSignature website.

Results

Clinical Characteristics of AOSD Patients

Among the initially enrolled 41 patients, 2 patients who had low nucleic acid quality and another with incomplete laboratory data were excluded from further analysis. Of the 38 patients with active AOSD, spiking fever ($\geq$39° C.), rash, arthralgia or arthritis, sore throat, liver dysfunction, and lymphadenopathy were noted in 37 (97.4%), 31 (81.6%), 30 (78.9%), 24 (63.2%), 20 (52.6%), and 14 (36.8%) patients respectively. As shown in Table 3, there were no significant differences in the age at entry or in proportion of female between AOSD patients and healthy controls (HC). 27 patients had systemic subtype and the other patients had chronic articular subtype of disease course.

TABLE 3

Demographic data and laboratory findings of patients with adult-onset Still's disease (AOSD) and healthy controls (HC)#

| Characteristics | AOSD-systemic subtype (n = 27) | AOSD-articular subtype (n = 11) | HC (n = 32) |
|---|---|---|---|
| Age at study entry, years | 37.5 ± 10.7 | 37.6 ± 12.0 | 38.3 ± 8.9 |
| Female proportion, n (%) | 23 (85.2%) | 9 (81.8%) | 24 (75.0%) |
| IL-1$\beta$ levels, pg/ml | 1.21 (0.62-5.27)** | 3.01 (1.30-20.8)*** | 0.08 (0.00-0.89) |
| IL-6 levels, pg/ml | 1035 (306-1205)** | 1126 (439-2021)** | 422 (95-972) |
| IL-17A levels, pg/ml | 148 (40-1317) | 264 (71-1358)* | 173 (25-345) |

TABLE 3-continued

Demographic data and laboratory findings of patients with
adult-onset Still's disease (AOSD) and healthy controls (HC)#

| Characteristics | AOSD-systemic subtype (n = 27) | AOSD-articular subtype (n = 11) | HC (n = 32) |
|---|---|---|---|
| IL-18 levels, pg/ml | 6279 (260-11074)*** | 2958 (576-7979)*** | 27.3 (5.2-94.7) |
| TNF-α levels, pg/ml | 37.8 (6.1-123.6)**§ | 245.7 (116.5-1813.5)*** | 5.5 (0.9-47.2) |

Data presented as mean ± SD, number (percentage), or median (interquartile range);
NA: not applicable;
IL: interleukin;
TNF-α: tumor necrosis factor-α.
*p < 0.05,
**p < 0.01,
***p < 0.001, vs. healthy controls, determined by Mann-Whitney U test.
§P < 0.01, AOSD-systemic subtype vs. AOSD-articular subtype, determined by Maim-Whitney U test.

LncRNA Expression Signature and Cytokine Profile in AOSD Patients and HC

By using qRT-PCR, the expression levels of the six lncRNAs ΔCT ($CT^{lncRNA}-CT^{GAPDH}$) of each individual subject in AOSD-systemic subtype, in AOSD-articular subtype, and in healthy controls (HC) are shown in FIG. 1a-1f. Compared with the medians of HC, the median ΔCT levels of MIAT seemed to be lower in both AOSD subtypes (FIG. 1a), and the median levels of THRIL ΔCT had a higher trend in both AOSD subtypes (FIG. 1b). However, none of the difference reached statistical significance as calculated by Kruskal-Wallis tests. As shown in Table 3 and FIG. 1, plasma levels of IL-1β, IL-6, IL-17A, IL-18, and TNF-α were significantly higher in AOSD patients than in HC. Of note, the differences of IL-6, IL-18 and TNF-α levels among groups had lower p values (p values for IL-6, IL-18 and TNF-α were all <0.01).

Figure 2:
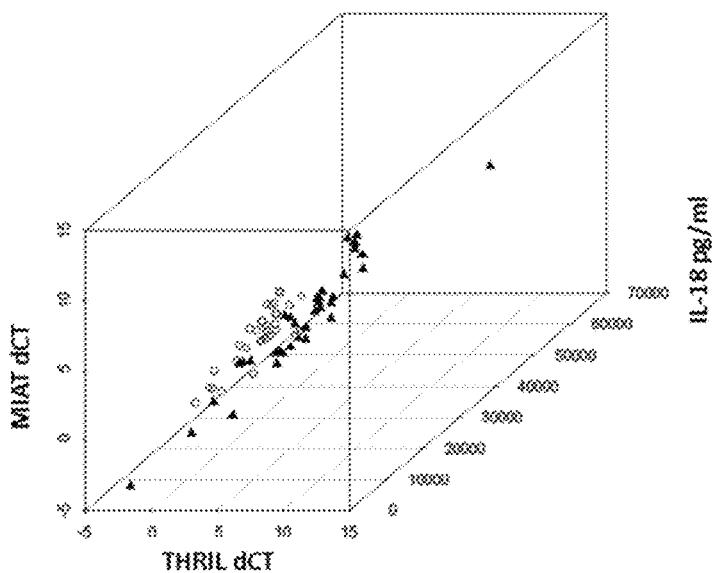
FIG. 2. Differentiation of AOSD patients from healthy controls by the expression signature of MIAT, THRIL, and IL-18. a. 3D-scatterplot demonstrating MIAT, THRIL and IL-18 levels of each sample. Circle: healthy controls; triangle: AOSD patients (both subtypes). b. Receiver operating characteristic (ROC) curve analysis of the AOSD prediction score (A score) derived from MIAT, THRIL and IL-18 expression levels. Area under the curve (AUC)=0.998 at the cutoff value >7.114, sensitivity=94.87%, and specificity=100% on predicting the diagnosis of AOSD.
Figure 2:
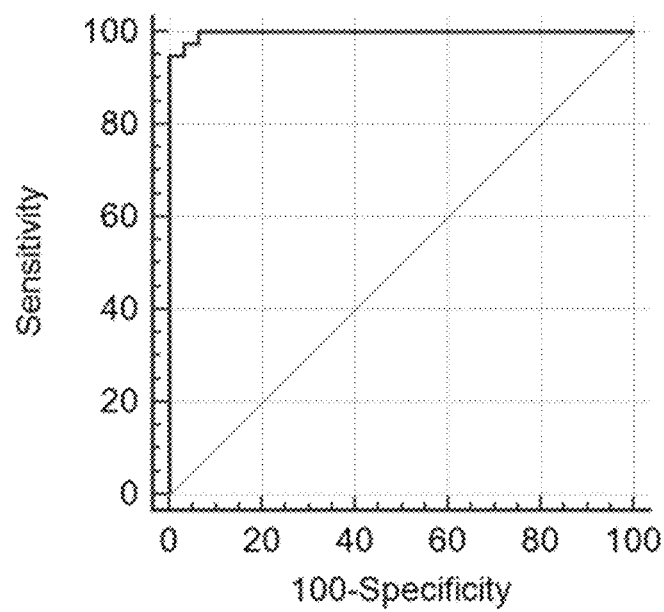

Establishment of Prediction Scores Using lncRNAs Expression Signatures and Cytokines To build up a lncRNA expression-based diagnostic model for AOSD, we further performed multiple regression analysis using ΔCT values of both MIAT and THRIL as variables to predict the occurrence of AOSD. The coefficient for MIAT was −1.43, p=0.003, and the coefficient for THRIL was 1.62, p=0.001. We also performed multiple regression analysis using IL-6, IL-18 and TNF-α levels for predicting AOSD, but only IL-18 reached statistical significance (p=0.027). The expression levels of MIAT, THRIL and IL-18 of each sample were projected onto a 3D scatterplot using the R software. As shown in FIG. 2a, AOSD samples could be best separated from control samples by a new set of putative biomarkers comprising MIAT, THRIL and IL-18 expression. Furthermore, 70% of the samples were randomly selected as the test dataset, and the other 30% of samples as the validation dataset to build a confusion matrix for evaluating the performance of the classification algorithm using this new set. The accuracies of test dataset and validation dataset for predicting AOSD were both 100%.

Therefore, we constructed a prediction equation to calculate a score (named as "A score") for the diagnosis of AOSD based on the coefficients and values of MIAT, THRIL and IL-18. The prediction equation is as follows: A score=1.62*THRIL ΔCT−1.43*MIAT ΔCT+0.02*IL-18 (pg/ml).

The ROC analysis of "A score" for diagnosing AOSD showed AUC of 0.998 at the cutoff value of 7.114, with sensitivity of 94.87%, and specificity of 100% (FIG. 2b). For the replication in a second cohort, an independent sample set of 16 patients with active AOSD were further collected. Application of our A score on the second AOSD cohort revealed a 100% correct classification rate at the same cutoff value (7.114).

Establishment of a Prediction Score for Differentiating AOSD Subtypes

Figure 3:
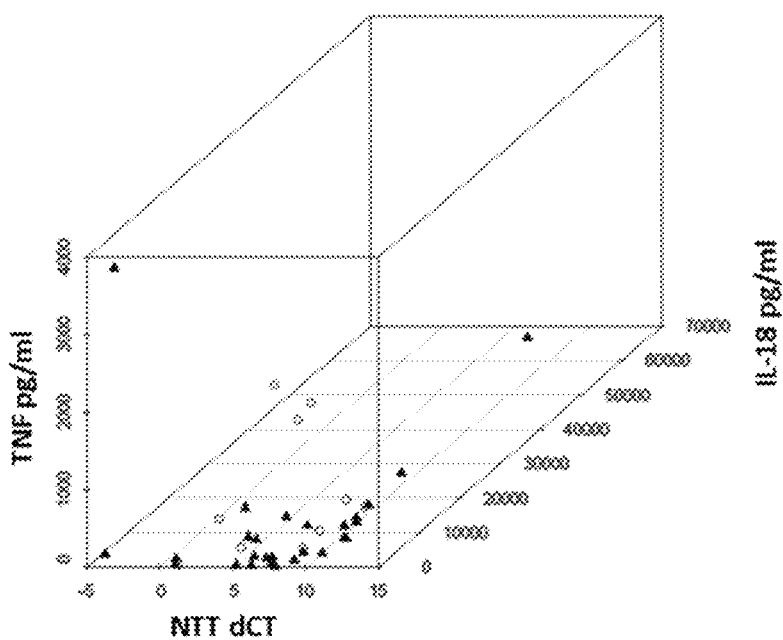
FIG. 3. Differentiation of AOSD subtypes of disease outcome by the expression signature of NTT and TNF-α. a. 3D-scatterplot demonstrating NTT, TNF-α and IL-18 expression levels of each sample. Circle: AOSD-arthritis subtype; triangle: AOSD-systemic subtypes. b. ROC curve analysis of the AOSD-subtype prediction score (B score) derived from NTT and TNF-α expression levels. AUC=0.855 at the cutoff value >0.266, sensitivity=66.7%, and specificity=90.9% on predicting AOSD-systemic subtype among AOSD patients.
Figure 3:
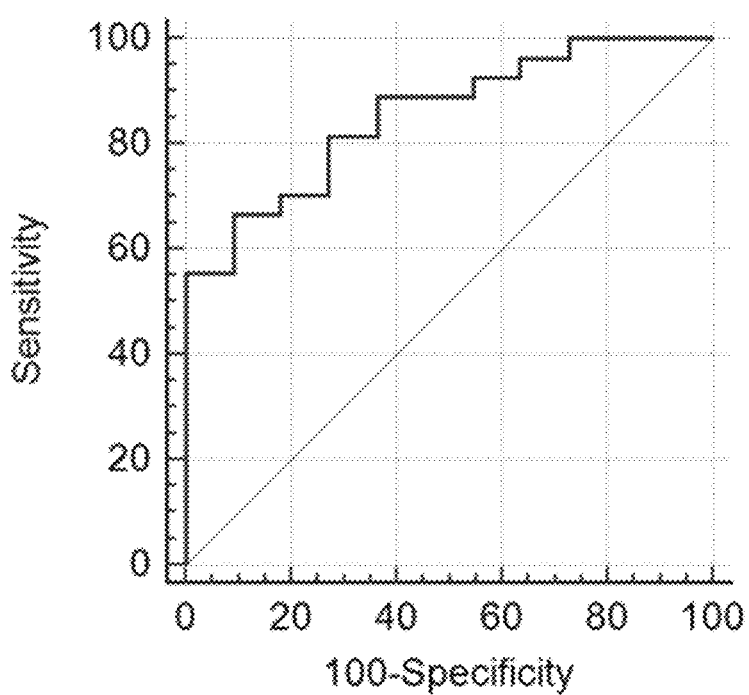

To further differentiate AOSD subtypes of disease course, the different combinations of lncRNA expression and cytokine levels of AOSD patients in the systemic subtype and articular subtype were plotted on 3D-scatterplots. The results showed that the expression of NTT ΔCT and TNF-α levels could best separated samples of AOSD systemic subtype from those of articular subtype (FIG. 3a). The R generalized linear model of confusion matrix comprising NTT ΔCT and TNF-α values for differentiating AOSD subtypes revealed an accuracy of 76.92% on the test dataset (70% of all samples), and an accuracy of 83.33% on the validation dataset (30% of all samples).

A prediction equation consisting of the coefficients obtained from regression analysis and expression values of NTT and TNF-α was established to calculate a score (named as "B score") for determining the disease courses of AOSD in a subject. The prediction equation is as follows: B score=0.22*NTT ΔCT−0.01*TNF-α (pg/ml).

The ROC analysis of "B score" on differentiating AOSD subtypes showed AUC of 0.855 at the cutoff value of 0.266, with sensitivity of 66.7% and specificity of 90.9% (FIG. 3b).

Correlation Studies of lncRNA, Cytokine Expressions and AOSD Disease Activity

Given that the six lncRNAs were selected based on their roles in immune regulation and inflammatory response, the correlation of lncRNAs or cytokines expression levels and disease activity scores in AOSD patients were examined. Interestingly, AOSD samples with lowest RMRP and PACERR expressions (RMRP ΔCT+PACERR ΔCT>17) have a high disease activity score (p=0.03, FIG. 4a). Plasma IL-18 values were also significantly correlated with AOSD disease activity ($r^2$=0.38, p<0.0001, FIG. 4b). However, the expression values of NTT, NEAT1, MIAT, RMRP, THRIL, and PACERR were not significantly correlated with plasma levels of cytokines. The expressions of each lncRNA did not significantly correlate with disease activity in either systemic- or articular-subtype of AOSD (FIG. 4c).

Figure 5:
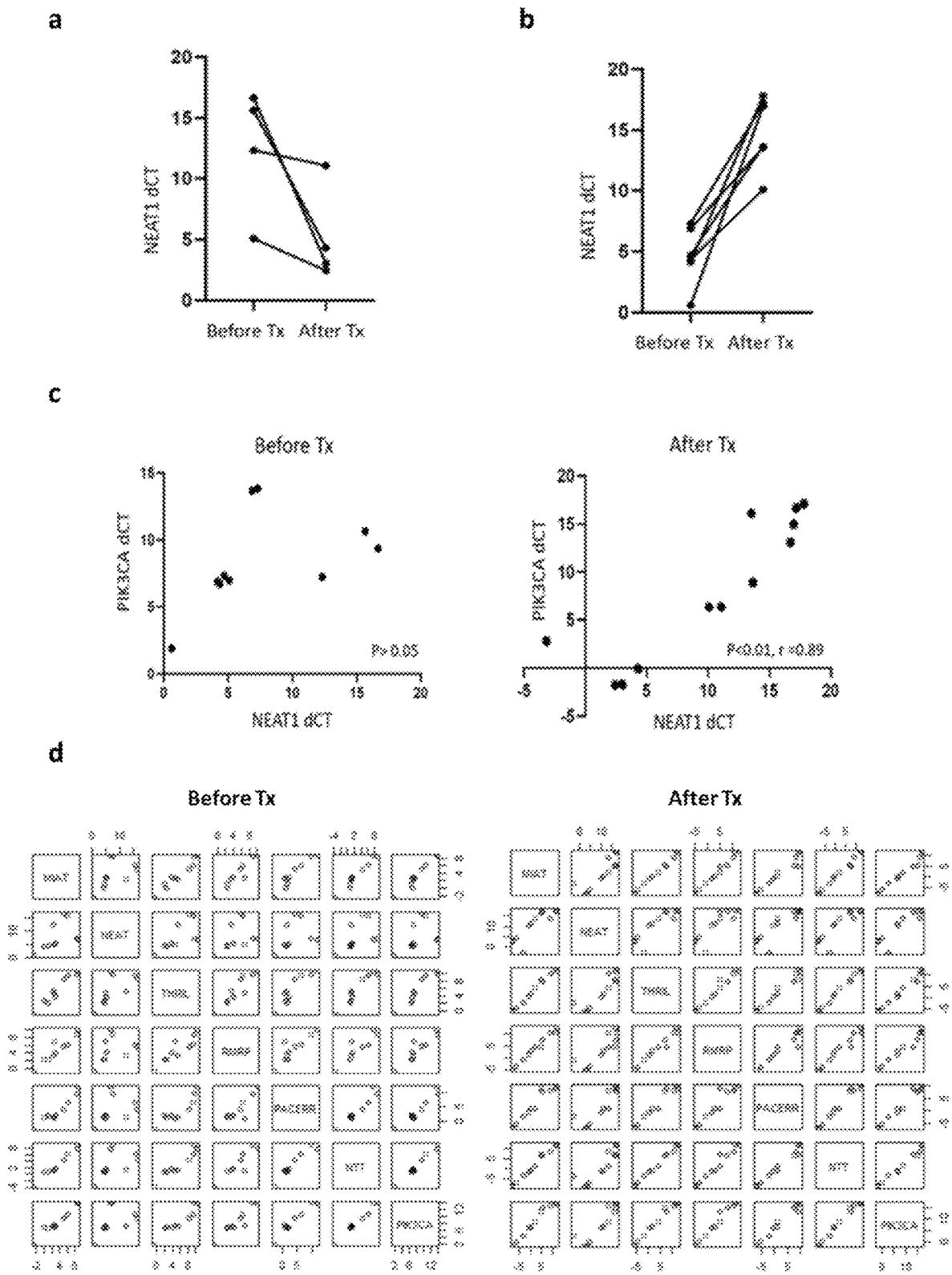
FIG. 5. Comparison of the lncRNA expression patterns in AOSD patients before and after therapy. a-b. The change in NEAT1 expression level in AOSD patients who received therapy with prednisolone or cyclosporin alone (a) or IL-6 receptor inhibitor, tocilizumab (b). Tx: treatment. c. Correlations of NEAT1 and PIK3CA dCT level before and after treatment (all treatments). d. Pairplots showing correlations between every two lncRNA expression and correlations of lncRNAs with PIK3CA dCT levels before and after treatments. The Pearson correlation coefficient and its p value were shown at the right lower corner of the graph.

Changes in Levels of lncRNAs Expression and Proinflammatory Cytokines in AOSD Patients after Therapy The change of the six lncRNAs expression and proinflammatory cytokines levels in 10 AOSD patients with available blood samples before and after 6-12 months of therapy were examined. As shown in FIG. 5a-b, NEAT1 expression was elevated after treatment with csDMARDs alone; while downregulation of NEAT1 expression was observed in AOSD patients treated with tocilizumab, IL-6 receptor inhibitor.

Figure 6:
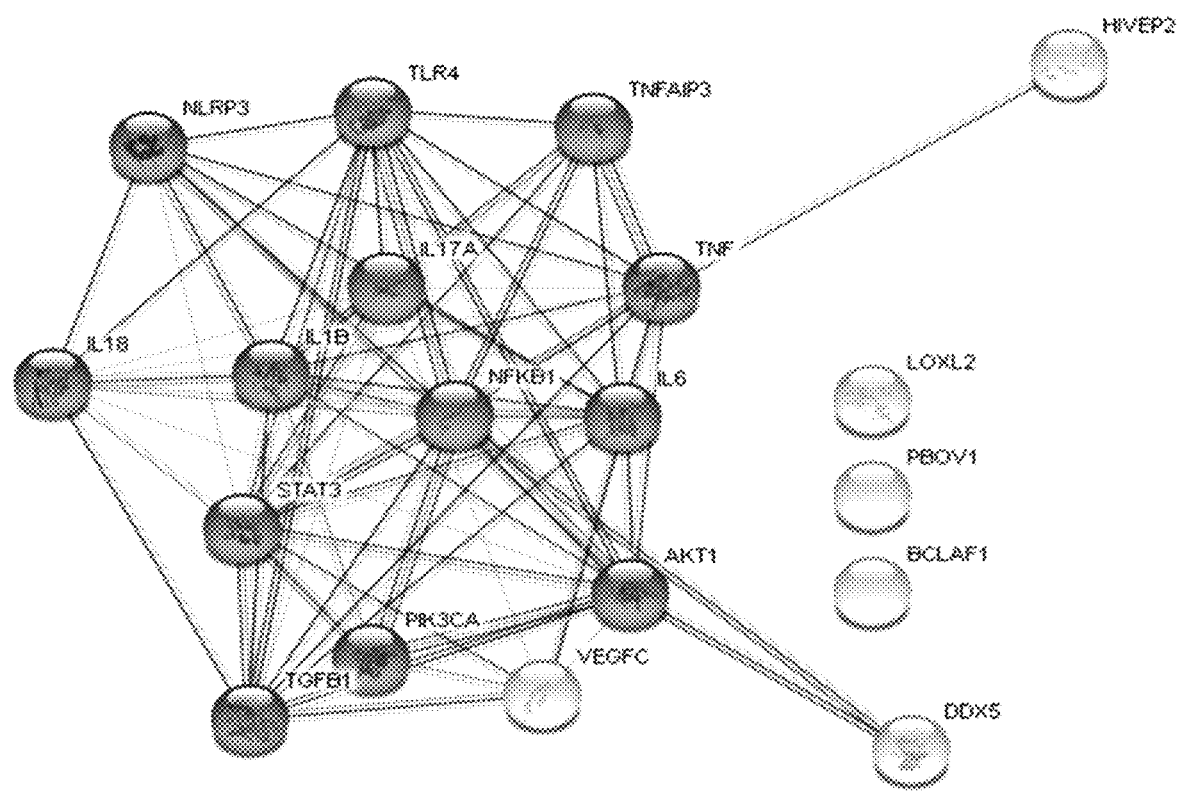
FIG. 6. Network analysis of interactions of lncRNA-related molecules using STRING (Protein-Protein Interaction Networks Functional Enrichment Analysis). Dim gray spots represent molecules in the enriched pathway of inflammatory response (GO:0006954).

Given that PIK3CA may be a downstream regulator of lncRNAs shown by network analysis (FIG. 6), a positive correlation between PIK3CA and NEAT1 was noted in patients after therapy (FIG. 5c, r=0.89, p<0.01). As shown in FIG. 5d, the positive correlations of PIK3CA with the 6 lncRNAs became more prominent after therapy.

LncRNA Expression Patterns on TLR-Ligand Stimulations in Monocytic Cell Line

Figure 4:
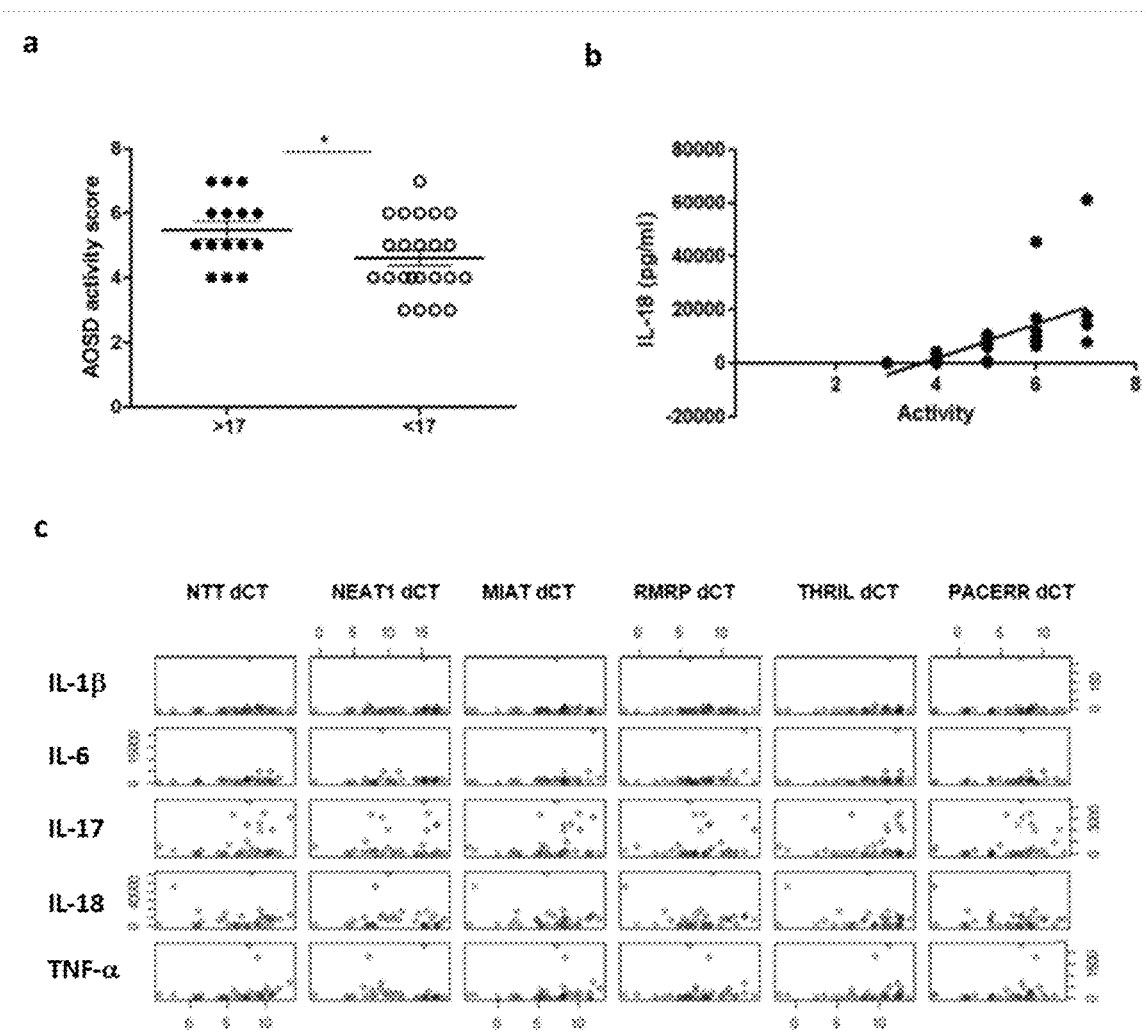
FIG. 4. Correlation of lncRNA expression levels with cytokines or AOSD disease activity. a. Association of low RMRP and PACERR expression with AOSD disease activity. All AOSD patients were grouped into (RMRP dCT+PACERR dCT)>17 or (RMRP dCT+PACERR dCT)<17, and the levels of disease activities were compared between the two groups by Mann-Whitney U test. b. Correlation of IL-18 level with AOSD disease activity (AOSD, n=38). $r^2=0.38$, $p<0.0001$ by linear regression analysis. c. Pairs plot showing scatterplots of between all pairs of lncRNA and cytokine expression levels in each AOSD patient sample (plotted by R software). *: $p<0.05$. Bars represent mean±SEM.
Figure 7:
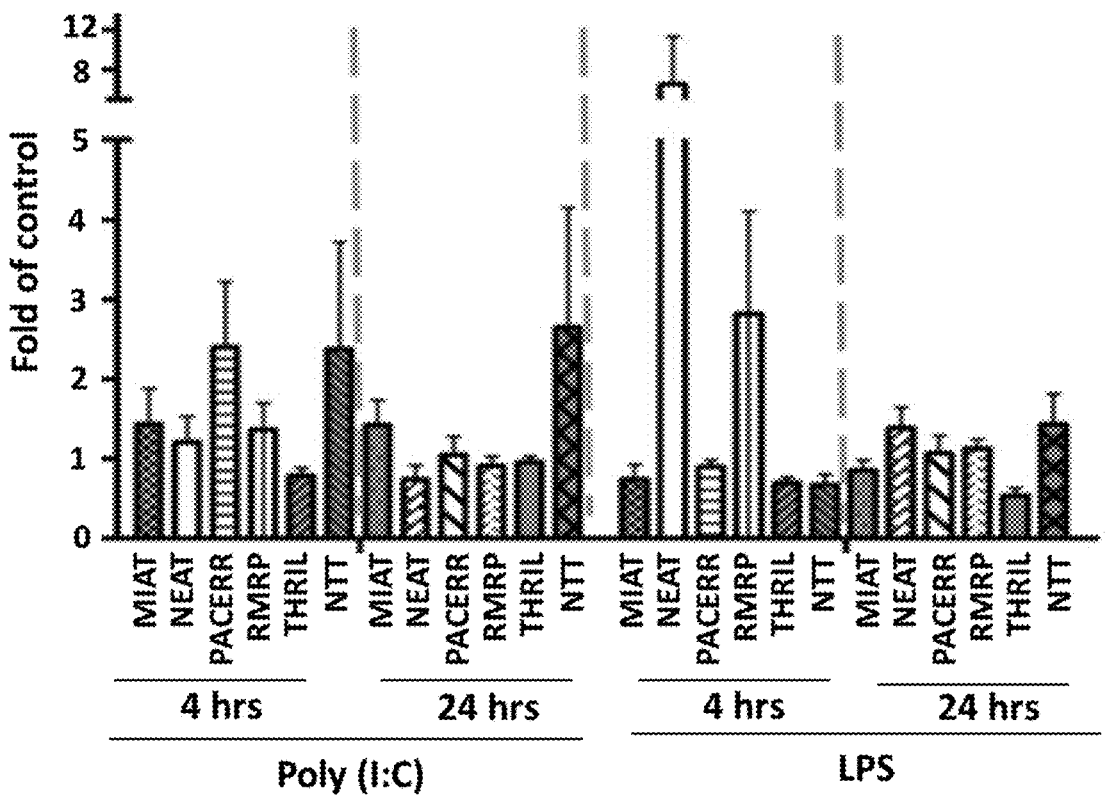
FIG. 7. LncRNAs expression patterns upon poly (I:C) or LPS stimulation in human monocytic cell line THP-1. THP-1 cells were stimulated with 50 µg/ml poly (I:C) or 100 ng/ml LPS for 4 hours or 24 hours. THP-1 cells cultured in LPS-free RPMI medium only for indicated time were used as controls for the respective experiments. The expression levels of the lncRNAs or PIK3CA were measured by real-time PCR. a. The expressions level of six lncRNAs. b. The expressions level of PIK3CA. The 4 h poly(I:C) stimulation: n=6-8; 4 h LPS stimulation: n=3-5; 24 h poly(I:C) stimulation: n=5-6; 24 h LPS stimulation: n=3-5. Bars represent mean±SEM.
Figure 7:
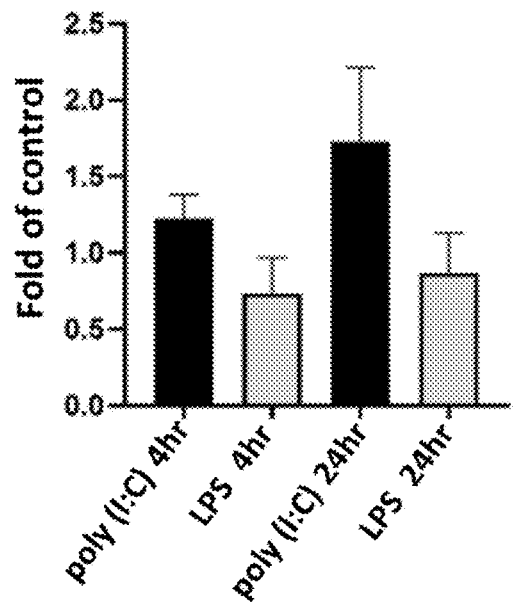

Since TLR3 activation has been reported to be involved in AOSD pathogenesis, the lncRNA expression patterns upon TLR3 ligand poly(I:C) and TLR4 ligand LPS stimulations in THP-1, a human monocytic cell line were examined. As shown in FIG. 4, after a 4-hour or 24-hour stimulation, poly(I:C) and LPS induced different lncRNA expression signatures. The increased MIAT and decreased THRIL levels in THP-1 cells stimulated with poly(I:C), which is similar to the change of lncRNA expression patterns in AOSD patients were observed. Moreover, MIAT downregulation combined with upregulations of NEAT1 and RMRP was detected in THP-1 cells treated with LPS. In addition, poly(I:C) upregulated NTT expression at 4-hour and 24-hour stimulation; while LPS increased NTT expression levels after 24-hours of stimulation (FIG. 7a). In addition, the results showed that increased PIK3CA expression levels in THP-1 cells stimulated with poly(I:C), but not with LPS (FIG. 7b).

Figure 8:
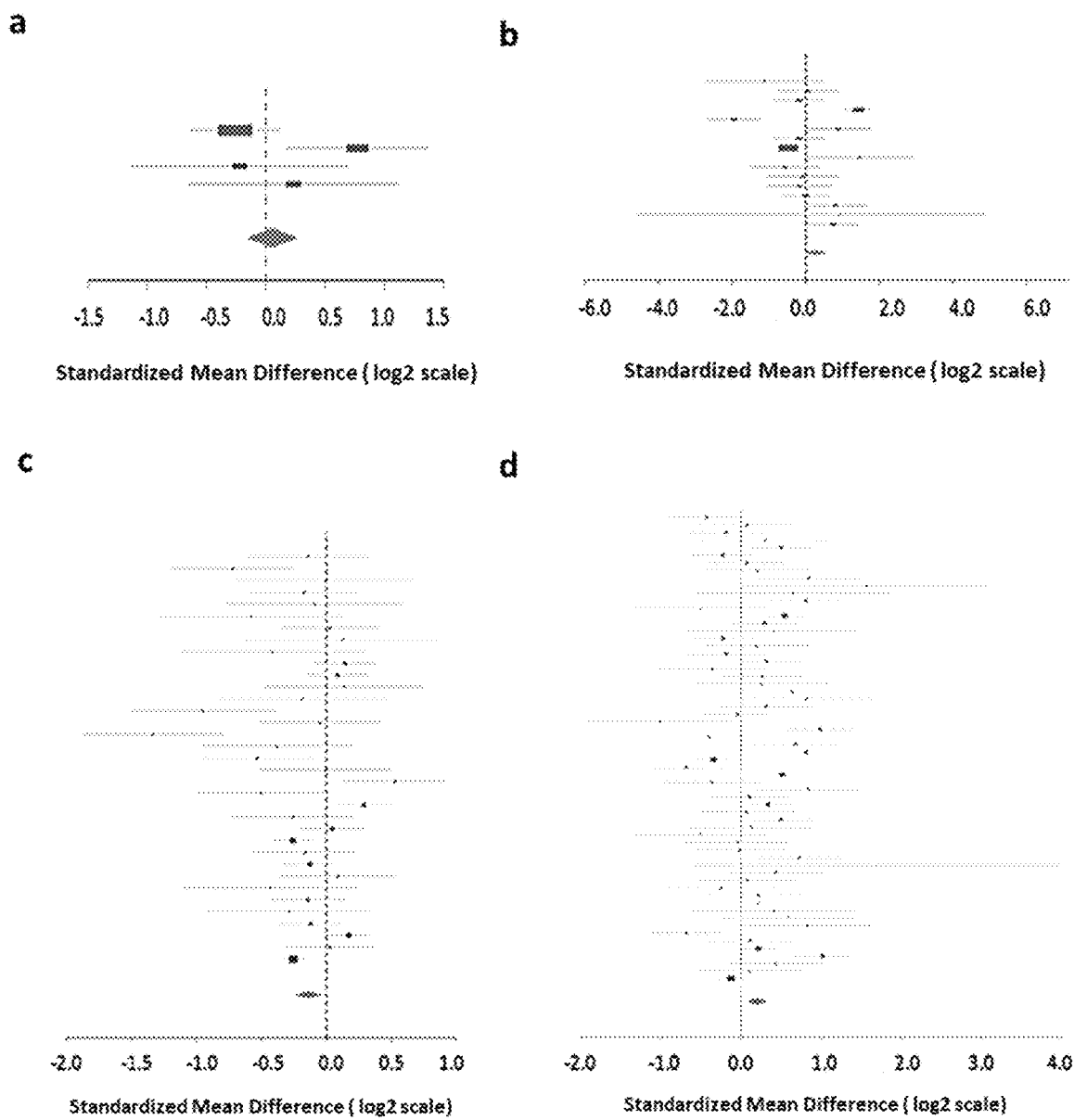
FIG. 8. MIAT and IL-18 expression in RA and SLE transcriptomes. a-b. Meta-transcriptomic analyses of MIAT (a) and IL-18 (b) expression in RA. c-d. Meta-transcriptomic analyses of MIAT (c) and IL-18 (d) expression in SLE. The meta-transcriptomic analyses were performed using the MetaSignature website (http://metasignature.stanford.edu/). Each box represents a disease cohort transcriptome dataset selected from the Gene Expression Omnibus (GEO) repository by the MetaSignature website.

Expression Signature of MIAT, THRIL and IL-18 in the Transcriptomes of RA, SLE, or Sepsis To investigate whether the lncRNA expression signature identified in AOSD patients is similar to the lncRNA expression pattern in other rheumatic diseases, meta-transcriptome analyses were performed on the transcriptome datasets in RA and SLE obtained from the Gene Expression Omnibus (GEO) repository using the MetaSignature website (http://metasignature.stanford.edu/). In AOSD patients' PBMCs, upregulation of MIAT and IL-18, together with the decreased expression of THRIL were observed. The value of THRIL was not available on RA or SLE transcriptome arrays. However, a meta-analysis of the expression of MIAT and IL-18 on RA and SLE transcriptome datasets revealed different signatures as compared with AOSD results. In RA, MIAT and IL-18 were not markedly elevated (FIG. 8a-8b). In SLE, the expression of MIAT was downregulated, while IL-18 was equivocally upregulated (FIG. 8c-8d).

Figure 9:
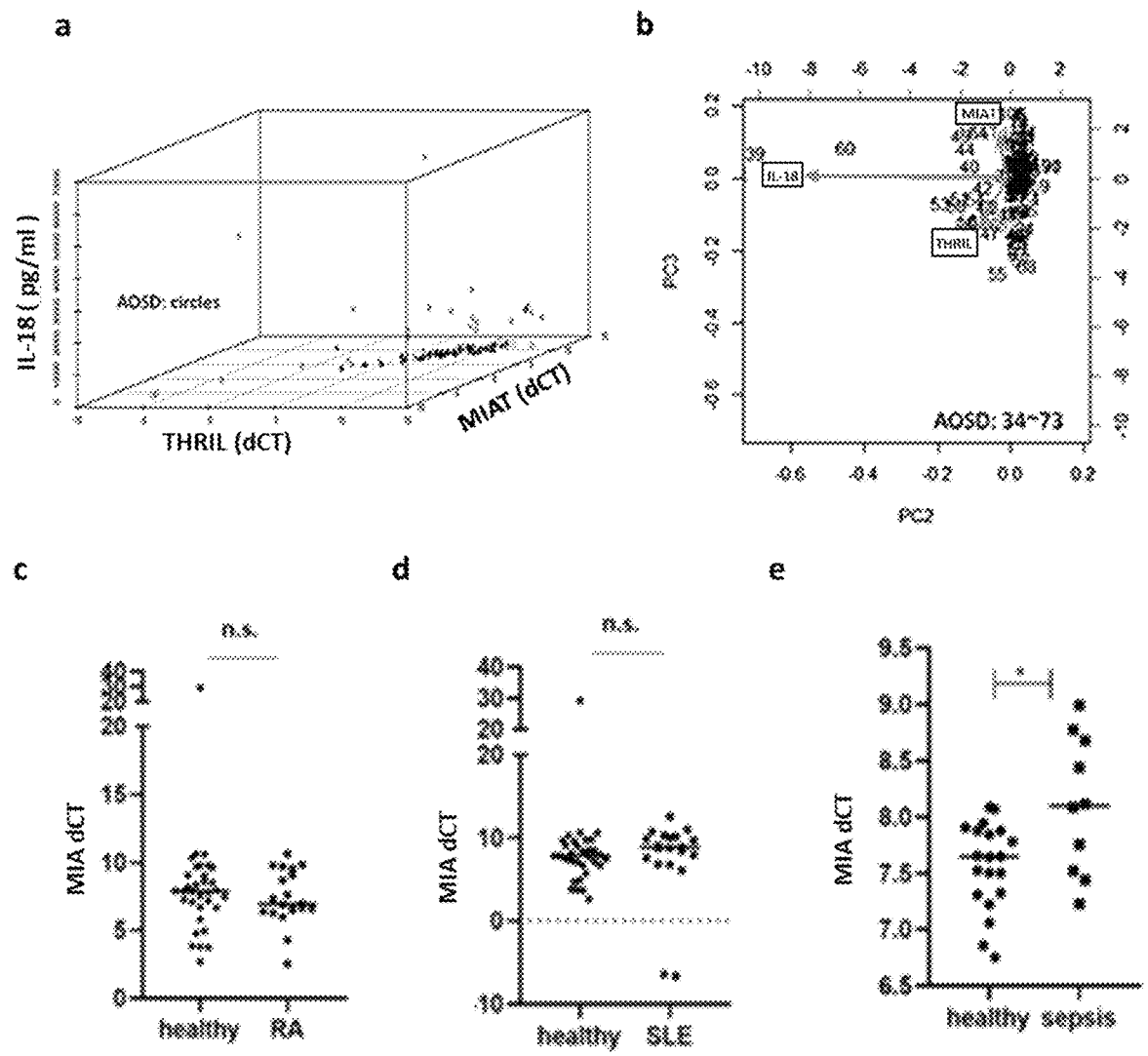
FIG. 9. Differentiating AOSD samples from RA and SLE samples using combined MIAT (dCT), THRIL (dCT) and IL-18 (pg/ml) expression patterns. a. 3D-scatterplot demonstrating MIAT (dCT), THRIL (dCT) and IL-18 (pg/ml) levels of each sample. Diamond: AOSD; cross: RA; triangle: SLE. b. Principle component analysis (PCA) of MIAT (dCT), THRIL (dCT) and IL-18 (pg/ml) values from PBMCs of AOSD, RA and SLE patients. c-d. MIAT dCT values in RA and SLE PBMCs as compared with healthy controls. e. Relative expression values of MIAT in sepsis and healthy control blood cells (GSE 28750 dataset). n.s. not significant, *p<0.05 by Mann-Whitney U tests.

Furthermore, additionally enrolled 20 SLE and 20 RA patients to investigate the six lncRNAs expression levels and proinflammatory cytokines. The results showed that AOSD could be separated from RA and SLE by plotting the combined THRIL, MIAT and IL-18 expression values onto a 3D scatter plot and a principle component analysis (PCA) plot (FIG. 9a-9b).

Figure 10:
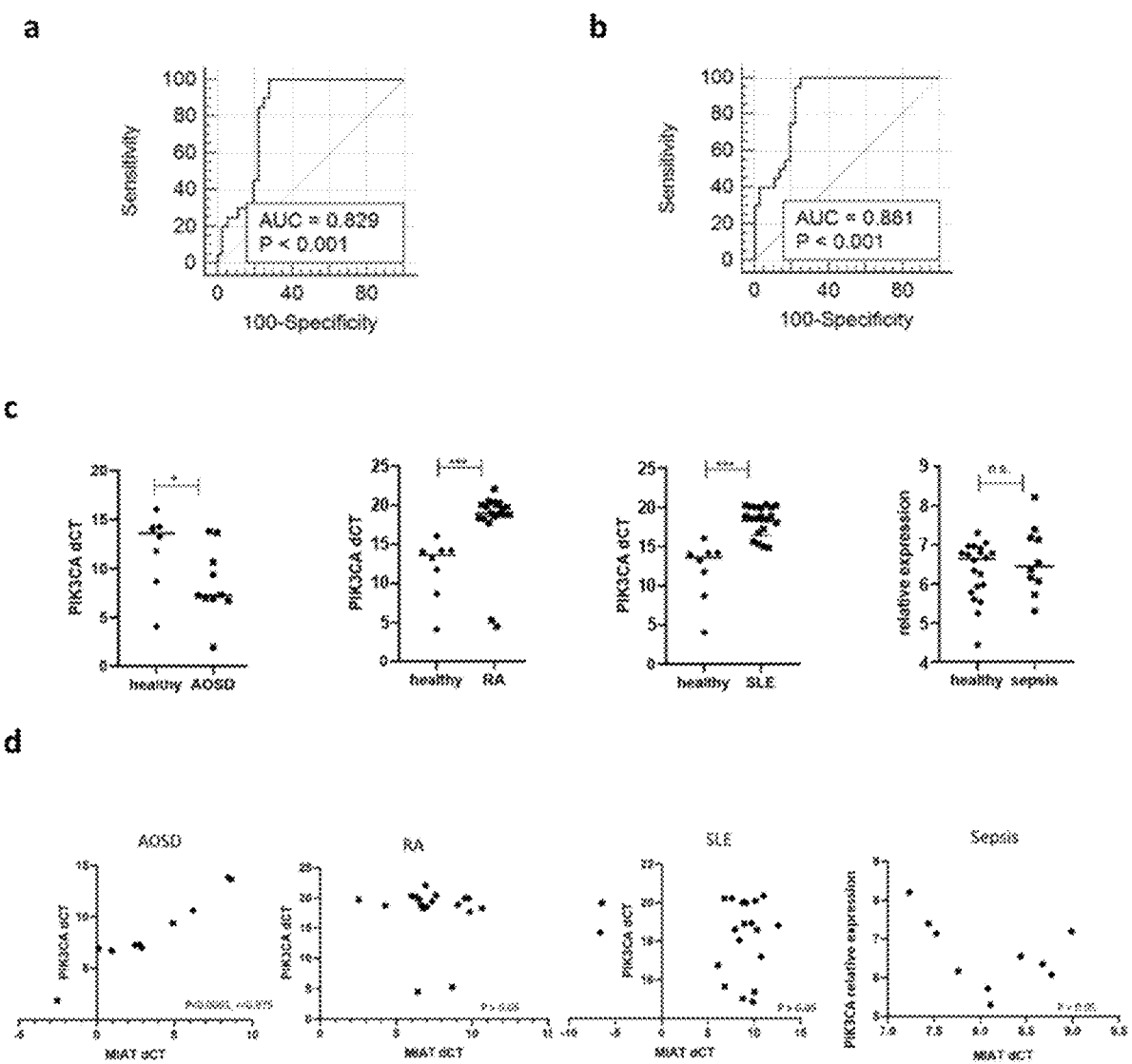
FIG. 10. Comparison of the lncRNA expression patterns in AOSD, RA, SLE and sepsis patients. a-b. Receiver operating characteristic (ROC) curve analysis of the AOSD prediction score (A score) on identifying RA from AOSD (a: AUC=0.829 at the cutoff value >12.57) or on identifying SLE from AOSD (b: AUC=0.881 at the cutoff value >11.39). c. PIK3CA expression levels in AOSD, RA, SLE or Sepsis compared to the levels in healthy control PBMCs. Lines represent medians. *p<0.05, ***p<0.001 by Mann-Whitney U tests. PIK3CA dCT was calculated by the subtraction of GAPDH Ct value. Sepsis microarray blood cell transcriptome dataset GSE28750 was collected from Gene Expression Omnibus (GEO). The relative expression levels of PIK3CA in sepsis and healthy control blood cells are shown. n.s.: not statistically significant by Mann-Whitney U test. d. Correlations of MIAT with PIK3CA expression in blood cells of patient with AOSD, RA, SLE or Sepsis. The Pearson correlation coefficient r/p value is shown at the right lower corner of the graph.

By using our A score, it also could distinguish RA and SLE patients from the AOSD group, with the AUC of 0.829 and 0.881 respectively, and the cutoff values were higher in detecting RA and SLE (at 12.57 and 11.39, respectively (FIG. 10a-10b).

Given no available blood samples from sepsis patients, the microarray data of a sepsis cohort GSE28750 (collected from the NCBI's Gene Expression Omnibus (GEO)) was re-analyzed. In GSE28750, it could be retrieved the expression data of the lncRNA MIAT, but not the value of THRIL. Unlike the results of AOSD, RA or SLE, the relative expression values of MIAT were significantly higher in sepsis blood samples compared with control (FIG. 1a and FIG. 9c-9e). Moreover, PIK3CA expression was evaluated in healthy, or patient with AOSD, RA, SLE or sepsis (Table 4 and Table 5). The results showed PIK3CA expression significantly higher in untreated AOSD patients compared with healthy controls (FIG. 10c), suggesting a potential pathogenic role of PIK3CA in AOSD. In contrast, the expression level of PIK3CA was lower in RA and SLE, and not significantly different in sepsis patients when compared with healthy controls. Interestingly, the expression level of PIK3CA were only positively correlated with MIAT expression in AOSD, but not in RA, SLE, or sepsis (FIG. 10d).

TABLE 4

The PIK3CA expression (ΔCT) in healthy or patient with AOSD, RA, or SLE.

| Subject | Health (n = 8) | AOSD (n = 11) | RA (n = 32) | SLE (n = 20) |
|---|---|---|---|---|
| PIK3CA (ΔCT) | 12.04 ± 3.63 | 8.46 ± 3.39 | 17.89 ± 4.57 | 18.31 ± 1.83 |

The data of ΔCT values presented as mean ± SD.

TABLE 5

The relative expression of PIK3CA compare with healthy and patient with sepsis.

| Subject | Health (n = 19) | sepsis (n = 10) |
|---|---|---|
| PIK3CA | 6.34 ± 3.0.72 | 6.61 ± 0.83 |

The data of relative expression presented as mean ± SD.

What is claimed is:

1. A method for detecting or diagnosing a subject suffering from Adult-onset Still's disease (AOSD), the method comprising the steps of:
   (a) providing a blood sample and a peripheral blood mononuclear cell from the subject;
   (b) detecting the expression level of a protein biomarker in the blood sample, wherein the protein biomarker is IL-18; detecting expression levels of a long non-coding ribonucleic acid (lncRNA) from the peripheral blood mononuclear cell, wherein the lncRNA comprises myocardial infarction associated transcript (MIAT) and TNFα and hnRNPL-related immunoregulatory lincRNA (THRIL);
   (c) calculating an A score of the detected IL18, MIAT and THRIL obtained in step (b) through a prediction equation, which is determined by performing a multiple regression analysis;
   (d) comparing the A score calculated in step (c) with a cutoff value, wherein the cutoff value is obtained by a Receiver Operator Characteristic (ROC) method, wherein the cutoff value corresponds to the area under an ROC curve (AUC) at its maximum, and the ROC method is established based on the expression of the lncRNA and IL-8 of AOSD patients and healthy subjects, wherein the A score being higher than the cutoff value indicates that the subject suffers from AOSD; and (e) administering an effective amount of AOSD-treating drugs to the subject.

2. The method according to claim 1, wherein the prediction equation is as follows:

A score=$1.62*$THRIL $\Delta$CT$-1.43*$MIAT $\Delta$CT$+0.02*$IL-18 (pg/ml), wherein CT represents a comparative threshold cycle, THRIL $\Delta$CT is: CT of THRIL–CT of GAPDH, and MIAT $\Delta$CT is: CT of MIAT–CT of GAPDH.

3. The method according to claim 1, wherein the cutoff value is between 5.85 to-7.12.

4. The method according to claim 1, further comprising detecting the expression level of phosphatidylinositol-4,5-bisphosphate 3-kinase catalytic subunit alpha (PIK3CA) in the peripheral blood mononuclear cells, wherein the PIK3CA gene expression being higher than a healthy individual indicates the subject is excluded from having systemic lupus erythematosus, rheumatoid arthritis or sepsis.

5. The method according to claim 4, wherein the healthy individual is an individual who does not have rheumatic diseases.

6. The method according to claim 1, wherein the blood sample is whole blood, serum or plasma.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Homo sapiens

<400> SEQUENCE: 1
ctggagaggg aggcatctaa                                        20

<210> SEQ ID NO 2
<211> LENGTH: 19
<212> TYPE: DNA

<213> ORGANISM: Homo sapiens

<400> SEQUENCE: 2
aactcatccc cacccacac                                                19

<210> SEQ ID NO 3
<211> LENGTH: 19
<212> TYPE: DNA
<213> ORGANISM: Homo sapiens

<400> SEQUENCE: 3
aacaggtgca cgtttcagg                                                19

<210> SEQ ID NO 4
<211> LENGTH: 20
<212> TYPE: DNA
<213> ORGANISM: Homo sapiens

<400> SEQUENCE: 4
tacacatgat gggacccaaa                                               20

<210> SEQ ID NO 5
<211> LENGTH: 19
<212> TYPE: DNA
<213> ORGANISM: Homo sapiens

<400> SEQUENCE: 5
cttggcctaa aagggatg                                                 19

<210> SEQ ID NO 6
<211> LENGTH: 20
<212> TYPE: DNA
<213> ORGANISM: Homo sapiens

<400> SEQUENCE: 6
gcacctttgg tctccttcac                                               20

<210> SEQ ID NO 7
<211> LENGTH: 19
<212> TYPE: DNA
<213> ORGANISM: Homo sapiens

<400> SEQUENCE: 7
agaagcgtat cccgctgag                                                19

<210> SEQ ID NO 8
<211> LENGTH: 18
<212> TYPE: DNA
<213> ORGANISM: Homo sapiens

<400> SEQUENCE: 8
gagaatgagc cccgtgtg                                                 18

<210> SEQ ID NO 9
<211> LENGTH: 21
<212> TYPE: DNA
<213> ORGANISM: Homo sapiens

<400> SEQUENCE: 9
tccacgggtc accaatataa a                                             21

<210> SEQ ID NO 10
<211> LENGTH: 18

```
<212> TYPE: DNA
<213> ORGANISM: Homo sapiens

<400> SEQUENCE: 10
cgtccctgca aattctgg                                                    18

<210> SEQ ID NO 11
<211> LENGTH: 19
<212> TYPE: DNA
<213> ORGANISM: Homo sapiens

<400> SEQUENCE: 11
ctctgacccg aagggtagg                                                   19

<210> SEQ ID NO 12
<211> LENGTH: 18
<212> TYPE: DNA
<213> ORGANISM: Homo sapiens

<400> SEQUENCE: 12
ctggcagctt tgctcctg                                                    18

<210> SEQ ID NO 13
<211> LENGTH: 21
<212> TYPE: DNA
<213> ORGANISM: Homo sapiens

<400> SEQUENCE: 13
tcatgcattg ttttgcaccc c                                                21

<210> SEQ ID NO 14
<211> LENGTH: 20
<212> TYPE: DNA
<213> ORGANISM: Homo sapiens

<400> SEQUENCE: 14
aatgggatag tgcctgagcc                                                  20

<210> SEQ ID NO 15
<211> LENGTH: 19
<212> TYPE: DNA
<213> ORGANISM: Homo sapiens

<400> SEQUENCE: 15
agccacatcg ctcagacac                                                   19

<210> SEQ ID NO 16
<211> LENGTH: 19
<212> TYPE: DNA
<213> ORGANISM: Homo sapiens

<400> SEQUENCE: 16
gcccaatacg accaaatcc                                                   19
```